US00PP23919P2

(12) United States Plant Patent
Psenner

(10) Patent No.: US PP23,919 P2
(45) Date of Patent: Sep. 24, 2013

(54) *LANTANA* PLANT NAMED 'LAN 876'

(50) Latin Name: *Lantana camara*
Varietal Denomination: LAN 876

(75) Inventor: Thomas Psenner, Bolzano (IT)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 13/385,286

(22) Filed: Feb. 10, 2012

(51) Int. Cl.
*A01H 5/00* (2006.01)

(52) U.S. Cl.
USPC ..... Plt./227

(58) Field of Classification Search
USPC ..... Plt./227
See application file for complete search history.

*Primary Examiner* — Kent L Bell
(74) *Attorney, Agent, or Firm* — C. A. Whealy

(57) ABSTRACT

A new and distinct cultivar of *Lantana* plant named 'LAN 876', characterized by its upright to outwardly spreading plant habit; freely branching growth habit; relatively large leaves; freely flowering habit; and large flowers that are initially yellow in color and become orange red in color with development.

1 Drawing Sheet

Botanical designation: *Lantana camara.*
Cultivar denomination: 'LAN 876'.

BACKGROUND OF THE INVENTION

The present invention relates to a new and distinct cultivar of *Lantana* plant, botanically known as *Lantana camara* and hereinafter referred to by the name 'LAN 876'.

The new *Lantana* plant is a product of a planned breeding program conducted by the Inventor in Bolzano, Italy. The objective of the breeding program is to create new rounded freely-flowering *Lantana* plants with attractive flower coloration.

The new *Lantana* plant originated from a cross-pollination made by the Inventor in 2007 in Bolzano, Italy of *Lantana camara* 'LAN 508', not patented, as the female, or seed, parent with *Lantana camara* 'Calippo Tutti Frutti', not patented, as the male, or pollen, parent. The new *Lantana* plant was discovered and selected by the Inventor as a single flowering plant from within the progeny of the stated cross-pollination in a controlled greenhouse environment in Bolzano, Italy in August, 2008.

Asexual reproduction of the new *Lantana* plant by vegetative cuttings in a controlled greenhouse environment in Bolzano, Italy since November, 2008, has shown that the unique features of this new *Lantana* plant are stable and reproduced true to type in successive generations.

SUMMARY OF THE INVENTION

Plants of the new *Lantana* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'LAN 876'. These characteristics in combination distinguish 'LAN 876' as a new and distinct *Lantana* plant:

1. Upright to outwardly spreading plant habit.
2. Freely branching growth habit.
3. Relatively large leaves.

4. Freely flowering habit.
5. Large flowers that are initially yellow in color and become orange red in color with development.

Plants of the new *Lantana* can be compared to plants of the female parent, 'LAN 508'. Plants of the new *Lantana* differ from plants of 'LAN 508' in the following characteristics:

1. Plants of the new *Lantana* are more compact than and not as vigorous as plants of 'LAN 508'.
2. Plants of the new *Lantana* and 'LAN 508' differ in flower color as plants of 'LAN 508' have yellow-colored flowers that become pink in color with development.

Plants of the new *Lantana* can be compared to plants of the male parent, 'Calippo Tutti Frutti'. Plants of the new *Lantana* differ from plants of 'Calippo Tutti Frutti' in the following characteristics:

1. Plants of the new *Lantana* are more vigorous than and not as compact as plants of 'Calippo Tutti Frutti'.
2. Plants of the new *Lantana* are more outwardly spreading than and not as upright as plants of 'Calippo Tutti Frutti'.
3. Plants of the new *Lantana* and 'Calippo Tutti Frutti' in flower color as plants of 'Calippo Tutti Frutti' differ have red purple-colored flowers.

Plants of the new *Lantana* can be compared to plants of the *Lantana camara* 'Bante Rossa', disclosed in U.S. Plant Pat. No. 18,148. Plants of the new *Lantana* differ from plants of 'Bante Rossa' in the following characteristics:

1. Plants of the new *Lantana* are more vigorous than and not as compact as plants of 'Bante Rossa'.
2. Plants of the new *Lantana* and 'Bante Rossa' differ in flower color as plants of 'Bante Rossa' have purple pink and yellow-colored flowers.

BRIEF DESCRIPTION OF THE PHOTOGRAPHS

The accompanying colored photographs illustrate the overall appearance of the new *Lantana* plant showing the colors as true as it is reasonably possible to obtain in colored reproductions of this type. Colors in the photographs may differ slightly from the color values cited in the detailed botanical description which accurately describe the colors of the new *Lantana* plant.

The photograph at the bottom of the sheet comprises a side perspective view of a typical flowering plant of 'LAN 876' grown in a container.

The photograph at the top of the sheet is a close-up view of a typical flowering plant of 'LAN 876'.

DETAILED BOTANICAL DESCRIPTION

The aforementioned photographs and following observations and measurements describe plants grown during the summer in 15-cm containers in an outdoor nursery in Bonsall, Calif. under commercial practices typical of commercial *Lantana* production. During the production of the plants, day temperatures ranged from 29° C. to 37° C., night temperatures ranged from 15° C. to 21° C. and light levels ranged from 8,000 to 10,000 foot-candles. Plants were pinched two times and were ten weeks old when the photographs and the description were taken. In the following description, color references are made to The Royal Horticultural Society Colour Chart, 2007 Edition, except where general terms of ordinary dictionary significance are used.

Botanical classification: *Lantana camara* 'LAN 876'.

Parentage:

*Female, or seed, parent.*—*Lantana camara* 'LAN 508', not patented.

*Male, or pollen, parent.*—*Lantana camara* 'Calippo Tutti Frutti', not patented.

Propagation:

*Type*.—By vegetative cuttings.

*Time to initiate roots, summer*.—About ten days at 16° C.

*Time to initiate roots, winter*.—About 14 days at 16° C.

*Time to produce a rooted young plant, summer*.—About 18 days at 16° C.

*Time to produce a rooted young plant, winter*.—About 21 days at 16° C.

*Root description*.—Fleshy; thin; white in color.

*Rooting habit*.—Moderately freely branching; medium density.

Plant description:

*Plant and growth habit*.—Upright and outwardly spreading plant habit; vigorous growth habit.

*Plant height*.—About 20.5 cm.

*Plant diameter*.—About 30 cm by 37 cm.

Lateral branch description:

*Branching habit*.—Freely branching habit with about three to four primary lateral branches per plant; each primary lateral branch with potentially two secondary lateral branches developing at each node; pinching enhances lateral branch development.

*Length*.—About 21 cm.

*Diameter*.—About 3.5 mm.

*Internode length*.—About 3.2 cm.

*Strength*.—Strong.

*Texture*.—Pubescent; coarse.

*Color*.—Close to 146C.

Foliage description:

*Arrangement*.—Opposite, simple.

*Length*.—About 6 cm.

*Width*.—About 3.8 cm.

*Shape*.—Elliptic to lanceolate.

*Apex*.—Broadly acute.

*Base*.—Obtuse with attenuate tendencies.

*Margin*.—Serrate.

*Texture, upper and lower surfaces*.—Pubescent; coarse, rough.

*Venation pattern*.—Pinnate; arcuate.

*Color*.—Developing leaves, upper surface: Close to 146A. Developing leaves, lower surface: Close to 147B. Fully expanded leaves, upper surface: Close to 147A; venation, close to 146C. Fully expanded leaves, lower surface: Close to 147B; venation, close to 146D.

*Petiole*.—Length: About 1.8 cm. Diameter: About 2 mm. Texture, upper and lower surfaces: Pubescent. Color, upper and lower surfaces: Close to 146C.

Flower description:

*Flower arrangement and flowering habit*.—Solitary tubular flowers arranged in terminal and axillary hemispherical umbels; flowers face mostly upward or outward; freely flowering habit with about 42 flowers developing per inflorescence.

*Natural flowering season*.—Plants of the new *Lantana* flower continuously from spring until frost in the autumn in Southern California; plants begin flowering about ten weeks after planting.

*Flower longevity on the plant*.—About two to three days; flowers not persistent.

*Fragrance*.—Faint, fruity, raspberry-like.

*Inflorescence height*.—About 1.5 cm.

*Inflorescence diameter*.—About 4 cm.

*Flowers*.—Appearance: Flared trumpet, corolla fused, four-parted. Diameter: About 9 mm by 11 mm. Depth (height): About 1.5 cm. Throat diameter: About 1 mm. Tube diameter: About 1.5 mm. Tube length: About 1.1 cm.

*Flower buds*.—Length: About 1.1 cm. Diameter: About 2 mm. Shape: Elongate, oblong. Color: Close to N34C.

*Corolla*.—Arrangement: Single whorl of four fused petals. Petal lobe length: About 5 mm. Petal lobe width: About 5 mm. Petal lobe shape: Rounded. Petal lobe apex: Rounded. Petal margin: Entire to slightly erose. Petal texture, upper surface: Smooth, glabrous; velvety. Petal texture, lower surface: Pubescent. Color: When opening, upper surface: Close to 12A. When opening, lower surface: Close to 11C. Fully opened, upper surface: Close to 12A; with development, color shifts to 31A to 31B and eventually becoming closer to N34C. Fully opened, lower surface: Close to 12C; with development, color shifts to 35C to 35D. Throat: Close to 11B. Tube: Close to 1C.

*Calyx*.—Appearance: Short and narrow tubular calyx with four fused sepals. Length: About 2 mm. Diameter: Less than 1 mm. Sepal apex: Acute. Sepal margin: Entire. Sepal texture, inner surface: Smooth, glabrous. Sepal texture, outer surface: Pubescent. Sepal color, inner and outer surfaces: Close to 145C.

*Peduncles*.—Length: About 3.8 cm. Diameter: About 1.5 mm. Strength: Strong. Texture: Sparsely pubescent. Color: Close to 146B.

*Reproductive organs*.—Stamens: Quantity and arrangement: Four per flower, adnate to floral tube. Filament length: About 6 mm. Filament color: Close to 145C. Anther shape: Oval. Anther length: Less than 1 mm.

Anther color: Close to 4A. Pollen amount: Scarce. Pollen color: Close to 4B. Pistils: Quantity: One per flower. Pistil length: About 4 mm. Stigma shape: Oval. Stigma color: Close to 145C. Style length: About 3.5 mm. Style color: Close to 157A. Ovary color: Close to 145B. Fruits and seeds: Fruit and seed development have not been observed on plants of the new *Lantana*.

Garden performance: Plants of the new *Lantana* have been observed to have good garden performance and to tolerate wind, rain and temperatures ranging from about 1° C. to about 35° C.

Pathogen & pest resistance: Plants of the new *Lantana* have not been observed to be resistant to pests and pathogens common to *Lantana* plants.

It is claimed:

1. A new and distinct *Lantana* plant named 'LAN 876' as illustrated and described.

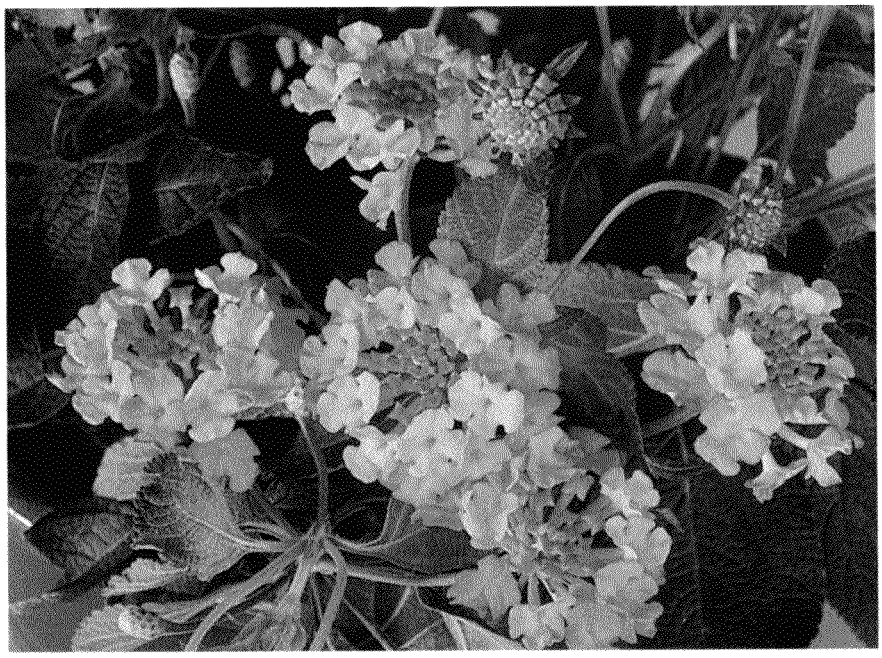
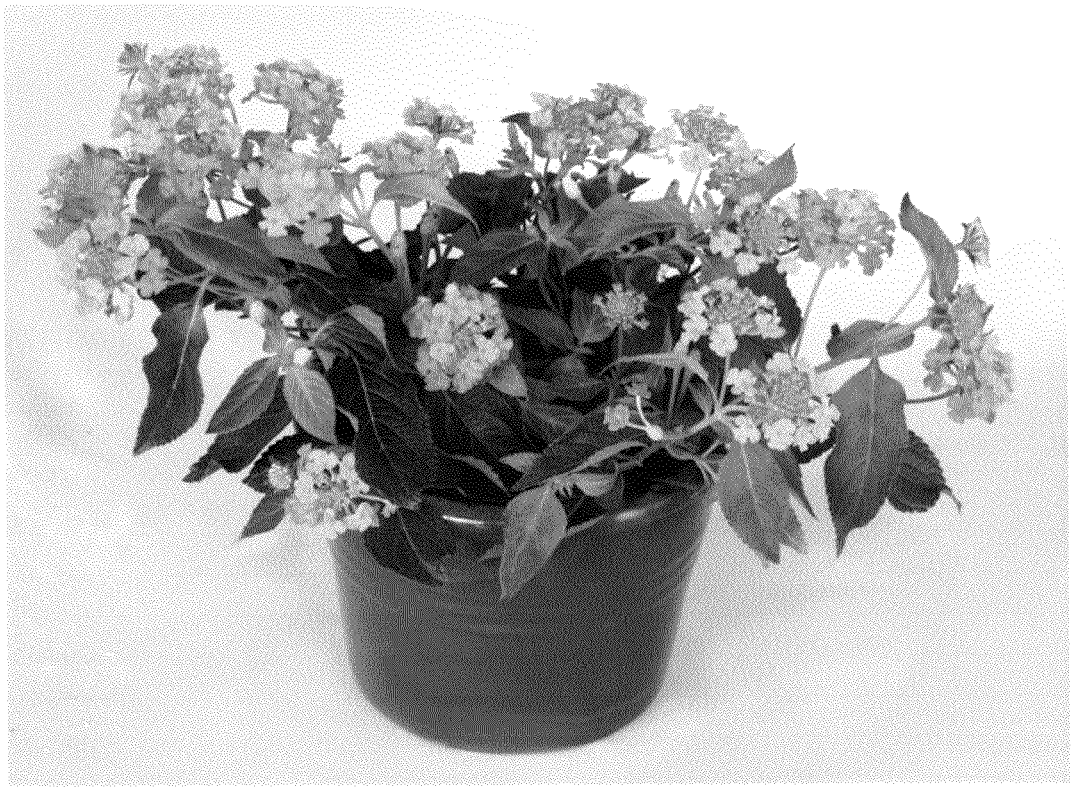

* * * * *